United States Patent
Chen et al.

(10) Patent No.: US 10,983,133 B2
(45) Date of Patent: Apr. 20, 2021

(54) DIAGNOSIS AND TREATMENT OF KAWASAKI DISEASE

(71) Applicant: Academia Sinica, Taipei (TW)

(72) Inventors: Yuan-Tsong Chen, Taipei (TW); Jer-Yuarn Wu, Taipei (TW); Tai-Ming Ko, Taipei (TW); Ho-Chang Kuo, Kaohsiung (TW); Jeng-Sheng Chang, Taichung (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 15/327,280

(22) PCT Filed: Jul. 23, 2015

(86) PCT No.: PCT/US2015/041687
§ 371 (c)(1),
(2) Date: Jan. 18, 2017

(87) PCT Pub. No.: WO2016/014761
PCT Pub. Date: Jan. 28, 2016

(65) Prior Publication Data
US 2017/0153250 A1    Jun. 1, 2017

Related U.S. Application Data

(60) Provisional application No. 62/028,633, filed on Jul. 24, 2014.

(51) Int. Cl.
| | |
|---|---|
| *A61K 39/395* | (2006.01) |
| *G01N 33/68* | (2006.01) |
| *C07K 16/00* | (2006.01) |
| *A61K 31/56* | (2006.01) |
| *A61K 39/00* | (2006.01) |

(52) U.S. Cl.
CPC ......... *G01N 33/6893* (2013.01); *A61K 31/56* (2013.01); *A61K 39/395* (2013.01); *C07K 16/00* (2013.01); *G01N 33/6863* (2013.01); *G01N 33/6869* (2013.01); *A61K 2039/505* (2013.01); *G01N 2333/522* (2013.01); *G01N 2333/54* (2013.01); *G01N 2333/5418* (2013.01); *G01N 2333/7056* (2013.01); *G01N 2333/70578* (2013.01); *G01N 2800/328* (2013.01)

(58) Field of Classification Search
None
See application file for complete search history.

(56) References Cited

U.S. PATENT DOCUMENTS

| 5,075,236 A | 12/1991 | Yone et al. |
| 2009/0304680 A1 | 12/2009 | Kuijpers et al. |
| 2011/0189698 A1 | 8/2011 | Burns |
| 2013/0316921 A1 | 11/2013 | Cohen et al. |
| 2014/0161791 A1 | 6/2014 | Kentsis et al. |

FOREIGN PATENT DOCUMENTS

| WO | WO 2010/025393 | 3/2010 |
| WO | WO 2012/142409 | 10/2012 |
| WO | WO 2014/043397 | 3/2014 |

OTHER PUBLICATIONS

Shikishima et al. Chemokines in Kawasaki disease: measurement of CCL2, CCL22 and CXCL10. Asian Pac J Allergy Immunol. Sep. 2003;21(3):139-43.*
Freeman et al. Kawasaki disease: summary of the American Heart Association guidelines. Am Fam Physician. Oct. 1, 2006;74(7): 1141-8.*
Gotsch et al. Maternal serum concentrations of the chemokine CXCL 10/IP-10 are elevated in acute pyelonephritis during pregnancy . J Matern Fetal Neonatal Med. Oct. 2007;20(10):735-44.*
Antonelli et al. High levels of circulating CXC chemokine ligand 10 are associated with chronic autoimmune thyroiditis and hypothyroidism. J Clin Endocrinol Metab. Nov. 2004;89(11): 5496-9.*
Singhal et al. Primary treatment of kawasaki disease with corticosteroids. J Clin Diagn Res. May 2014; 8(5): PD04-5.*
Chang et al "Detection of Chemokines in Patients with Kawasaki Disease and Henoch-Schonlein Purpura and its Clinical Significance" Journal of JiLin University (Medicine Edition) vol. 33, pp. 148-150, 2007.
Jia et al "The T Helper Type 17/Regulatory T Cell Imbalance in Patients with Acute Kawasaki Disease" Clinical and Experimental Immunology vol. 162, pp. 131-137, 2010.
Wright et al "Treatment of Immune Globulin-Resistant Kawasaki Disease with Pulsed Doses of Corticosteroids" The Journal of Pediatrics vol. 128, pp. 146-149, 1996.
Zhang et al "CD40L Expression on the CD4+T-Cells in Children with Kawasaki Disease and its Correlation with Coronary Artery Lesion" 2010.
Lee et al., "Two new susceptibility loci for Kawasaki disease identified through genome-wide association analysis." Nature Genetics, 2012; 44:522-5.
Kamisago et al "Changes in Serum Cytokines and Chemokines in Kawasaki Disease" 45th Annual Meeting of Japanese Society of Pediatric Cardiology and Cardiac Surgery, 2009.
Chen et al "Change in Plasma Level of Soluble E-Selectin and +A561C Polymorphisms in Children with Kawasaki Disease" International Journal of Rheumatic Diseases vol. 13, pp. 59-60, 2010.
Wang et al "Expression of CD40 Ligand on CD4+T-Cells and Platelets Correlated to the Coronary Artery Lesion and Disease Progress in Kawasaki Disease" Pediatrics vol. 111, pp. 140-147, 2003.

* cited by examiner

*Primary Examiner* — Dong Jiang
(74) *Attorney, Agent, or Firm* — Cesari & McKenna, LLP (57) ABSTRACT

Described is a method of diagnosing, treating, or monitoring a treatment for Kawasaki disease in a subject. The method includes detecting the level of a biomarker in a sample obtained from the subject, the biomarker being IL-7F, sCD40L, MPIF-1, E-selectin, IP-10, or IL-33. The level is compared to a cut-off level. Also described is a kit for carrying out the method.

8 Claims, 5 Drawing Sheets

DIAGNOSIS AND TREATMENT OF KAWASAKI DISEASE

CROSS REFERENCE TO RELATED APPLICATION

This application is the National Stage of International Application No. PCT/US2015/041687, filed on Jul. 23, 2015, which claims priority to U.S. Provisional Application No. 62/028,633, filed on Jul. 24, 2014. The content of both applications are hereby incorporated by reference herein in their entirety.

BACKGROUND

Kawasaki disease (KD), a multisystem inflammatory condition observed in younger children, can cause acute vasculitis, most notably affecting the coronary arteries. Without treatment, approximately 20-25% of children with KD develop coronary artery abnormalities (CAAs). Intravenous immunoglobulin (IVIG) treatment can reduce the incidence of CAAs to approximately 5%, but early detection is necessary.

KD diagnosis is difficult, especially at the early stage. Currently, KD diagnosis is based on clinical symptoms, including fever for ≥5 days, bilateral conjunctival injection without exudate, polymorphous exanthema, changes in the lips and mouth (erythema and cracking of lips, strawberry tongue, and diffuse injection of oral and pharyngeal mucosae), changes in the extremities (erythema and edema of the hands and feet), and cervical lymphadenopathy (≥1.5 cm in diameter). However, overlapping clinical features and laboratory parameters between KD and other conditions make definitive diagnosis difficult, and no specific laboratory tests are available.

Therefore, identification of specific biomarkers to facilitate KD diagnosis by laboratory analysis would be valuable for preventing serious KD sequelae, especially CAAs.

SUMMARY

Described herein is a method of diagnosing Kawasaki disease in a subject. The method includes detecting the level of a biomarker in a sample from a subject suspected of having Kawasaki disease, the biomarker being IL-7F, sCD40L, MPIF-1, E-selectin, IP-10, or IL-33; and comparing the level to a cut-off level; wherein the subject is determined to have Kawasaki disease if the level is higher or lower than the cut-off level. In one embodiment, the biomarker is IP-10 and the subject is determined to have Kawasaki disease if the level is higher than the cut-off level. The sample can be obtained from the subject within 0 to 10 days (e.g., with 5 days) of the onset of a fever in the subject.

Further, a method of treating Kawasaki disease in a subject is described herein. The method includes detecting a first level of a biomarker in a first sample from a subject suspected of having Kawasaki disease, the biomarker being IL-7F, sCD40L, MPIF-1, E-selectin, IP-10, or IL-33, wherein the first level is higher or lower than that of a cut-off level; and administering a treatment for Kawasaki disease to the subject. In one embodiment, the biomarker is IP-10 and the first level is higher than the cut-off level. The treatment can be intravenous immunoglobulin (IVIG) or IVIG and a steroid. The first sample can be obtained from the subject within 0 to 10 days (e.g., with 5 days) of the onset of a fever in the subject. The method can further include obtaining a second sample from the subject after the treatment is administered; detecting the level of the biomarker in the second sample; and continuing the treatment or administer a different treatment if the level in the second sample is higher than the cut-off level.

Also disclosed herein is a method of monitoring a treatment of Kawasaki disease in a subject. The method includes detecting a first level of a biomarker in a first sample obtained from the subject at a first time point before or during the treatment, the biomarker being IL-7F, sCD40L, MPIF-1, E-selectin, IP-10, or IL-33; detecting a second level of the biomarker in a second sample obtained from the subject at a second time point; comparing the first level and the second level; and making a treatment decision based on the comparison. The biomarker can be IP-10 and the treatment can be intravenous immunoglobulin (IVIG).

In any of the above methods, the sample can be a bodily fluid sample (e.g., a blood, serum, plasma, cerebrospinal fluid, urine, or saliva sample). An immune assay can be used to detect the level of the biomarker in the sample. For example, the immune assay can be ELISA, protein array, flow cytometry, multiplex immunoassays built on magnetic beads, western blot, dot blot, or ELISPOT. A cut-off plasma level of 1,318 pg/mL for IP-10 can be used in any of the above methods. In one embodiment, the patient population is Han Chinese.

A kit for diagnosing Kawasaki disease or monitoring a treatment for Kawasaki disease in a subject is also described herein. The kit can include an agent (e.g., an antibody) or device (e.g., a test trip, solid support, chip, or plate) for detecting the level of a biomarker. The biomarker can be IL-7F, sCD40L, MPIF-1, E-selectin, IP-10, or IL-33.

The details of one or more embodiments are set forth in the description below.

BRIEF DESCRIPTION OF THE DRAWINGS

FIG. 1 is a set of graphs showing protein levels during the acute phase of Kawasaki disease (KD). Plasma cytokine levels were measured in non-KD febrile controls (n=20) and KD patients (n=37) using the Bio-Plex system. The levels of plasma E-selectin, MPIF-1, and IP-10 identified from the protein array were determined by enzyme-linked immunosorbent assay in the febrile controls (n=20) and KD cases (n=37). The p values of IL-17F, IL-33, sCD40L, E-selectin, MPIF-1, and IP-10 were $1.5 \times 10^{-2}$, $7 \times 10^{-3}$, $2.8 \times 10^{-2}$, $8.6 \times 10^{-3}$, $2.3 \times 10^{-8}$, and $4.1 \times 10^{-11}$, respectively. Each dot represents the average of 3 analyses with variation <5% standard deviation from a single individual. *, $p<0.05$; , $p<0.01$, *, $p<0.001$; unpaired Student's t-test.

FIG. 3 is a graph showing plasma levels of IP-10 in the blinded validation study. Plasma IP-10 levels in the validation study (patients were <6 years old), which included febrile controls (C–F, n=37), incomplete KD patients (K–I, n=3), and KD patients (K, n=20), are determined using enzyme-linked immunosorbent assay. Error bars indicate the standard deviation from triplicate values.

DETAILED DESCRIPTION

It was unexpectedly discovered that the levels of certain biomarkers in subjects with KD are different from those in subjects with non-KD febrile conditions.

The biomarkers include IL-17F (Genbank Accession No. NP_443104), IL-33 (Genbank Accession No. NP_001186570), sCD40L (Genbank Accession No. NP_001289682), CCL23/MPIF-1 (Genbank Accession No. NP_665905), E-selectin (Genbank Accession No. NP_000441), and CXCL10/IP-10 (Genbank Accession No. NP_001556). The levels of IL-7F, sCD40L, MPIF-1, E-selectin, and IP-10 in KD patients were found to be higher than those in non-KD febrile subjects. The level of IL-33 in KD patients was lower than that in non-KD febrile subjects.

Thus, the levels of one or more of the biomarkers in a sample from a subject suspected of having KD (e.g., a subject showing symptoms of KD) can be detected and compared with their corresponding predetermined cut-off levels to determine whether the subject has KD. For example, if the level of IP-10 in the subject is higher than the corresponding cut-off level, it indicates that the subject has KD. Any of the biomarkers described herein can be used in combination with other diagnostic tests, biomarkers, or risk factors for KD to diagnose KD.

The sample can be a bodily fluid sample, e.g., a blood, serum, plasma, cerebrospinal fluid, urine, or saliva sample. The level of a biomarker in the sample can be determined using various methods, e.g. ELISA, protein array, flow cytometry, multiplex immunoassay built on magnetic beads, western blot, dot blot, or ELISPOT. In one exemplary method, a plasma or blood sample from a subject is spotted onto a filter paper, which can be dried and stored. The dried blood or plasma spot can then be used in ELISA to detect and quantify the level of the biomarker in the sample. See, e.g., Aabye et al., PLoS ONE, 7(6): e39228, June 2012. Antibodies that specifically recognize the above-described biomarkers are commercially available or can be generated using methods known in the art.

A predetermined cut-off level of a biomarker, representing the level of the same biomarker in a KD-free subject, can be determined based on the representative levels of the biomarker in groups of KD patients and KD-free subjects. KD-free subjects can include subjects with diseases or conditions that have overlapping clinical features and/or laboratory parameters with KD (e.g., prolonged fever, skin rashes, juvenile rheumatoid arthritis, certain viral and bacterial infections such as scarlet fever and toxic shock syndrome, and those conditions shown in Table 2 below). Suitable statistical analysis is applied to the obtained biomarker levels to determine a cut-off level that distinguishes KD patients from KD-free subjects, in particular KD-free subjects with conditions that are clinically similar to KD.

The biomarkers described herein (e.g., IP-10) can be used for early diagnosis of KD. For example, the level of a biomarker in a subject suspected of having KD can be detected within 0 to 10 days (e.g., less than 3 days, less than 4 days, less than 5 days, or less than 10 days) of the onset of fever in the subject. The detected biomarker level is then compared to the corresponding cut-off level to determine whether the subject has KD. As noted above, early diagnosis and therefore early intervention can prevent serious complications of KD.

Some KD patients do not show all of the typical symptoms of KD. The above-described method can be used for diagnosis of such cases of KD, i.e., incomplete or atypical KD.

After a subject has been determined to have KD using one or more of the above-described biomarkers, a treatment for KD can be administered to the subject. Early treatment reduces the subject's risk of coronary complications. IVIG has been shown to reduce fever and the risk of developing coronary abnormalities in a patient. In addition, aspirin can be given to control the fever. Some patients may require a second dose of IVIG to reduce the fever. Some patients are non-responsive to IVIG. In those cases, other treatments can be administered to the subjects. Such alternative treatments include anti-TNF-α antibodies (e.g. Infliximab) and IVIG in combination with a steroid.

Any of the above-described biomarkers can also be used to monitor a treatment of KD. The level of a KD biomarker in a patient undergoing a KD treatment (e.g., IVIG) can be determined at various time points, e.g., before the treatment and at one or more time points within 1 week after initiation of the treatment. During the course of the treatment, a change in the biomarker level trending toward its corresponding cut-off level indicates that the treatment is effective. For example, a lower level of IP-10 in the patient at one time point as compared to the level at an earlier time point indicates that the treatment is effective. If the biomarker level at a later time point is equal to or not significantly different from the level at an earlier point (e.g., before or right after initiation of the treatment), it indicates that the treatment should be continued (e.g., another dose of IVIG that is equal or higher than the previous one) or an alternative treatment should be administered. In other words, the levels of a KD biomarker in the subject during the course of the treatment can be used to make treatment decisions (e.g., to continue or stop the treatment, or to administer a different treatment).

Further, any of the above-described biomarker can be used to assess the efficacy of a candidate compound or treatment for KD. The level of a KD biomarker can be determined before, during, and or/after administration of the compound or treatment to a subject.

A kit for diagnosing or monitoring a treatment of KD can include an agent or device (e.g., a test strip, solid support, or plate) for detecting the level of a KD biomarker (e.g., IP-10). The agent can be an antibody specific for the KD biomarker.

The device can also include (e.g., coated with) an antibody specific for the KD biomarker.

The specific example below is to be construed as merely illustrative, and not limitative of the remainder of the disclosure in any way whatsoever. Without further elaboration, it is believed that one skilled in the art can, based on the description herein, utilize the present disclosure to its fullest extent. All publications cited herein are hereby incorporated by reference in their entirety. Further, any mechanism proposed below does not in any way restrict the scope of the claims.

EXAMPLE

We enrolled 214 children with fever and clinical features suggestive of KD. Of those, only 100 were diagnosed with KD. Their plasma samples were globally analyzed for cytokines, chemokines, and cell adhesion molecules using an unbiased, large-scale, quantitative protein array. This study was conducted in 3 stages: discovery, replication, and blinded validation. During the discovery phase [n(KD)=37, n(control)=20], the expression of interleukin-17F, sCD40L, E-selectin, CCL23(MPIF-1), and CXCL10(IP-10) were upregulated during the acute phase in KD patients compared to that in the controls. A notable increase was observed in the IP-10 levels (KD, 3,037±226.7 pg/mL; control, 672±130.4 pg/mL; $p=4.1 \times 10^{-11}$). Receiver-operating characteristic analysis of the combined discovery and replication data [n(KD)=77, n(control)=77] showed that the IP-10 level had high area under the curve values (0.94 [95% confidence interval, 0.9055-0.9778]; sensitivity, 100%; and specificity, 77%). With 1,318 pg/mL as the optimal cut-off, the blinded validation study confirmed that the IP-10 levels were a good predictor of KD. With intravenous immunoglobulin treatment, the IP-10 levels returned to normal. The downstream receptor of IP-10, CXCR3, was activated in the T cells of acute KD patients.

The study was approved by the Institutional Review Board and the Ethics Committee of the Institution Review Board of the China Medical University Hospital, Kaohsiung Chang Gung Memorial Hospital, and Academia Sinica in Taiwan. Written informed consent was obtained from the subjects or their parents.

Patients

We enrolled 214 Han Chinese children with a fever and clinical features suggestive of KD. Of those, only 100 were eventually diagnosed with KD. The demographic and clinical characteristics of these KD children are shown in Table 1. Final diagnoses of the 114 children with non-KD are shown in Table 2.

The children participating in the study were recruited in Taiwan from medical centers in different geographical areas—the Chang Gung Memorial Hospital Systems including 4 hospitals in the southern and northern part of Taiwan and the China Medical University Hospital Medical Center, including three regional hospitals in the central part of Taiwan. KD was diagnosed using known clinical diagnostic criteria. See Newburger et al., Pediatrics. 2004; 114:1708-1733; and Kim and Dedeoglu, Curr Opin Pediatr. 2005; 17:695-702. Of the 100 KD patients, 37 were included in the study's discovery phase, 40 in the replication phase, and 23 in the blinded validation phase, which included 3 patients with incomplete presentation of KD (iKD was defined as the presence of ≤4 principal symptoms of the Japanese criteria). See Newburger et al., Circulation. 2004; 110:2747-2771.

TABLE 1

Demographic and Clinical Characteristics of Patients Enrolled in This Study

| Variable | KD (N = 100) | FC (N = 114) |
| --- | --- | --- |
| Age (years) | 1.7 ± 1.6 | 3.6 ± 2.9 |
| Sex (Male %) | 66% | 62% |
| White blood cells per μL | 13829.7 ± 4802.7 | 10733.6 ± 5227.5 |
| Glutamate oxaloacetate transaminase (U/L) | 84.7 ± 114.8 | 35.8 ± 12.6 |
| Glutamate-pyruvate transaminase (U/L) | 90.2 ± 100.7 | 20.3 ± 11.8 |
| Number of principal clinical features | 4 ± 1 | 2 ± 1 |
| Duration of fever (days) | 5 ± 2 | 5 ± 2 |
| Left main coronary artery (mm) | 2.19 ± 0.43 | N.A. |
| Right coronary artery (mm) | 1.94 ± 0.45 | N.A. |

All variable data are expressed as mean±standard deviation (SD). KD, Kawasaki disease; FC, febrile control.

TABLE 2

Final Diagnosis of 214 Pediatric Patients

| Final diagnosis | No. |
| --- | --- |
| Kawasaki disease | 100 |
| pneumonia | 27 |
| bronchiolitis | 18 |
| tonsillitis | 13 |
| sinusitis | 9 |
| enteritis | 8 |
| pharyngitis | 5 |
| herpangina | 5 |
| urinary tract infection | 6 |
| herpetic gingivostomatitis | 3 |
| viral infection (ie. Epstein-Barr virus and adenovirus) | 3 |
| pyelonephritis | 2 |
| scarlet fever | 2 |
| otitis media | 1 |
| pyuria | 2 |
| parotitis | 1 |
| suspect infectious mononucleosis | 1 |
| hyponatremia | 1 |
| fever of unknown origin | 7 |

Multiplex analysis and quantification of cytokines, chemokines, and cell adhesion molecules Fresh heparinized blood samples that were obtained from the study subjects were centrifuged at 2,000 g for 10 min. Then the plasma samples were aliquot and were stored at −80° C. for further analysis. Samples were run in duplicate using the Bio-Plex Pro™ Human Th-17 Cytokine Panel 15-Plex (Bio-Rad, Hercules, Calif., USA). The complete list of cytokines (IL-1β, IL-4, IL-6, IL-10, IL-17A, IL-17F, IL-21, IL-22, IL-23, IL-25, IL-31, IL-33, IFN-γ, sCD40L, and tumor necrosis factor [TNF]-α) was quantified in these cohorts, and their detection limits and reproducibility were provided in the product manual. Fifteen distinct sets of fluorescently dyed beads loaded with capture monoclonal antibodies specific for each cytokine were used. The signal was measured and quantified using the Bio-Plex Protein Array System (Bio-Rad). Assays were performed using Bio-Plex Protein Array System integrated with Bio-Plex Manager Software, version 3.0 (Bio-Rad). Reporter conjugate emission wavelengths were adjusted using the Bio-Plex Calibration Kit (Bio-Rad). Fluidics performance, consistent optical alignment, doublet discrimination, and identification of individual bead signatures were validated using the Bio-Plex Validation Kit, version 3.0 (Bio-Rad). For the initial screening, plasma from 6 KD patients was examined using human protein array (AAH-CYT-G8-8; Raybiotech Inc., Norcross, Ga., USA), which assesses 54 chemokines and CAMs to identify proteins showing an upregulated expression in KD. The complete chemokine/CAM names are available at the raybiotech.com website. The identified upregulated genes, namely, IL-9, IP-10, E-selectin, and MPIF-1, were further quantified in the remaining KD patients by using enzyme-linked immunosorbent assay (ELISA). The limits of detection for the E-selectin, MPIF-1, and IP-10 ELISA were 30 pg/mL, 7 pg/mL, and 8 pg/mL, respectively. The reproducibility (intra-assay: CV<10%; inter-assay: CV<12%) and specificity of IP-10 were validated; this ELISA kit shows no cross-reactivity with any of the cytokines tested. Dilution ranged from 1:2-1:20 according to the manufacturer's instructions (RayBiotech Inc.).

Flow Cytometry

The peripheral blood mononuclear cells were isolated from the heparinized blood by Ficoll-Isopaque density gradient separation (Pharmacia Fine Chemicals, Uppsala, Sweden) Immunophenotypic analyses were performed using distinct fluorochrome-conjugated monoclonal antibodies that recognize human CD3 (UCHT1; BD Biosciences, San Jose, Calif., USA) or CXCR3 (1C6/CXCR3; BD Biosciences). After the PBMCs cells were incubated with dilute antibody (1:200) for 1 h at room temperature, they were examined by multicolor flow cytometry using a FACS Calibur device (BD Biosciences). Data were obtained using CellQuest acquisition software (BD Biosciences), and 0.5-2.0×10$^6$ events were recorded for analysis in each experiment.

Statistical Analysis

Statistical significance was assessed using unpaired Student's t-test and the Prism4 software (GraphPad, San Diego, Calif., USA). Receiver-operating characteristic (ROC) curve analysis was performed using SAS software, version 9.3 (SAS Institute Inc., Cary, N.C., USA). The ROC curve plots sensitivity and 1—specificity and provides a summary of sensitivity and specificity across a range of cut-off points for a continuous predictor. Between-group differences were determined using analysis of variance and logical regression analysis. The optimal cut-off value of each candidate biomarker was determined as the sum of its maximum sensitivity and specificity.

Plasma Profile: The Discovery Study

Figure 1:
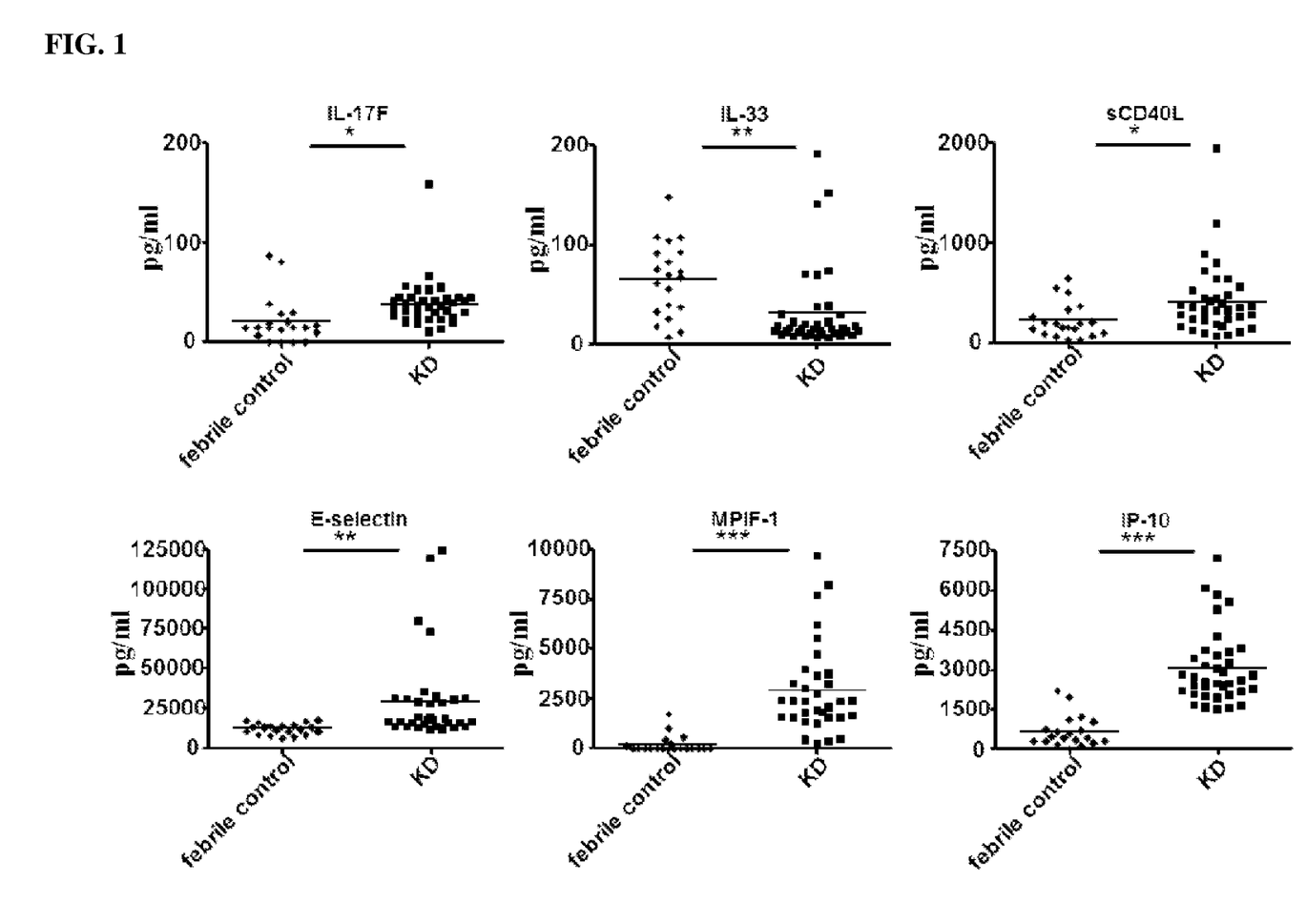

Using the cytokine multiplex system and protein array, 69 inflammatory cytokines were analyzed in total. In the initial screening, the plasma levels of 15 cytokines in 20 non-KD febrile controls and 37 KD patients were determined. The levels of IL-17F and sCD40L were significantly higher in the KD patients than in the febrile controls. See FIG. 1. Only one cytokine, IL-33, was found to be downregulated. See FIG. 1. While IL-1β was critical in the development of coronary lesions in a mouse model of KD, the plasma levels of IL-1β were not significantly elevated in the acute KD patients in the present study (data not shown).

For the remaining 54 inflammatory chemokines and CAMs, a proteomics approach was used to identify candidate biomarkers in a set of plasma samples obtained during the acute phase in 6 KD patients randomly selected from the discovery phase. These data were compared to those of the controls with a non-KD fever and skin rash. The average expression levels of 10 cytokines or CAMs were at least 1.3-fold higher in the KD patients than in the controls. See Table 3. Among these 10 proteins, IL-9, IP-10, E-selectin, and MPIF-1 showed an increase in the average expression of at least 2-fold in KD patients, and this result was found in all 6 patients tested. Further, the PDGF-AA, IL-2R-α, CD14, IGF-II, and Siglec-5 genes were downregulated in the acute-phase KD patients, showing at least a 1.8-fold decrease (<60%, data not shown) compared to the controls. ELISA was then conducted with a larger sample size (20 non-KD febrile controls and 37 KD patients) to quantify candidate biomarkers (IL-9, IP-10, E-selectin, and MPIF-1). Consistent with the protein array data for the acute-phase KD patients, there were significant increases in the IP-10, MPIF-1, and E-selectin levels. See FIG. 1. However, the increase in the IL-9 levels became insignificant when the sample size increased (data not shown). Among the 6 candidate KD biomarkers (IL-17F, IL-33, sCD40L, E-selectin, MPIF-1, and IP-10), IP-10 showed the most significant increase in KD patients (3,037±226.7 pg/mL) compared to the controls (672±130.4 pg/mL) (values in KD patients vs. values in non-KD febrile controls, p value=$4.1 \times 10^{-11}$). See FIG. 1.

TABLE 3

Signaling Intensities of the 10 Selected Candidate Genes Encoding Chemokines and CAMs from the Plasma of Acute-Phase Kawasaki Disease (KD) Patients.

|  | KD-1 | KD-2 | KD-3 | KD-4 | KD-5 | KD-6 | Ctr-1 | Ctr-2 | KD/Ctr fold |
| --- | --- | --- | --- | --- | --- | --- | --- | --- | --- |
| IL-9 | 336 | 253 | 5,749 | 668 | 774 | 967 | 174 | 149 | 9.02 |
| IP-10 | 4,316 | 2,562 | 2,200 | 6,595 | 3,348 | 10,314 | 596 | 913 | 6.48 |
| E-Selectin | 9,020 | 7,175 | 8,791 | 11,220 | 11,476 | 15,427 | 4,021 | 3,393 | 2.84 |
| MPIF-1 | 3,072 | 882 | 668 | 1,699 | 1,631 | 3,756 | 1,060 | 532 | 2.45 |
| SCF R | 2,421 | 2,419 | 2,606 | 9,067 | 2,578 | 7,584 | 2,561 | 1,899 | 1.99 |
| PDGF-AB | 5,645 | 6,649 | 6,144 | 12,379 | 8,837 | 13,695 | 5,632 | 4,178 | 1.81 |
| MMP-9 | 3,541 | 4,853 | 4,902 | 1,673 | 5,661 | 6,850 | 2,026 | 3,273 | 1.73 |
| ALCAM | 3,491 | 2,839 | 3,070 | 4,505 | 3,725 | 5,923 | 2,919 | 2,189 | 1.54 |
| L-Selectin | 13,597 | 14,850 | 14,208 | 20,070 | 16,264 | 25,435 | 13,621 | 11,460 | 1.39 |
| ICAM-2 | 32,272 | 29,906 | 37,391 | 57,141 | 25,626 | 32,476 | 26,188 | 27,011 | 1.35 |

All tests were performed in duplicate. Internal negative controls were used to determine the cut-off rate for a positive signal. Six KD patients and 2 control (Ctr) subjects were screened using protein arrays. Ctr-1 was a pediatric subject with a non-KD fever. Ctr-2 was a normal healthy subject. Only the KD/Ctr ratios (the average of KD patients/average of ctr cases) of chemokines and CAMs exceeding 1.3 are shown.

IP-10 Levels: The Replication Study and Combined Studies

Figure 2:
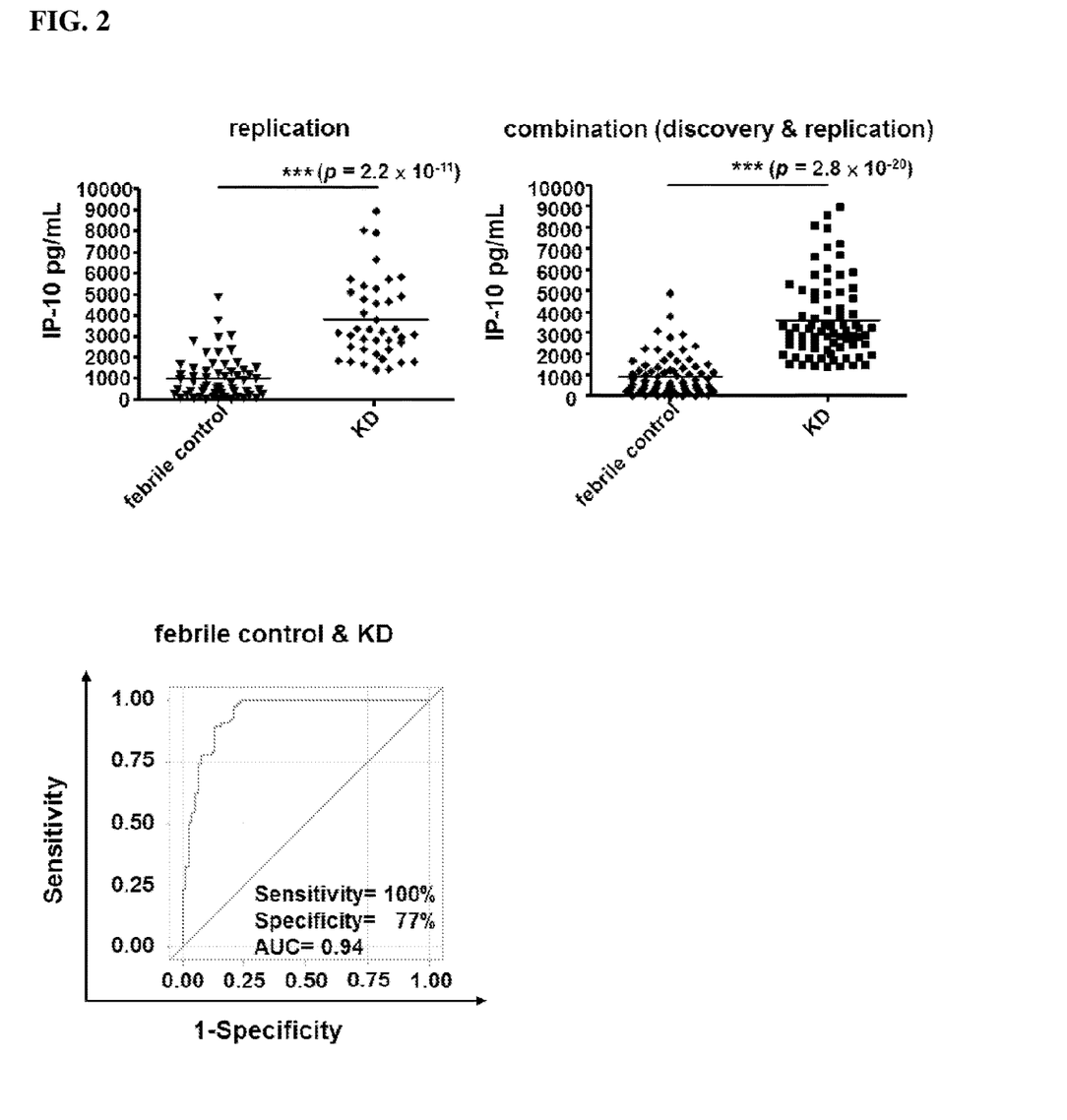
FIG. 2 is a set of graphs showing the combined data of the febrile controls and KD patients from the discovery and replication studies and the receiver operating characteristic (ROC) curve for the predictive model of Kawasaki disease with plasma levels of IP-10. Plasma IP-10 levels were determined in the febrile controls (n=57) and KD patients (n=40) by using enzyme-linked immunosorbent assay (ELISA). Those in the febrile controls (n=77) and KD cases (n=77) are also measured using ELISA. ***, $p<0.001$, unpaired Student's t-test. Each dot represents the average of 3 determinations with variation <5% (standard deviation/average) from a single individual. On the basis of the combination data, ROC curves of plasma IP-10 levels in KD patients are plotted against the febrile controls. The optimal cut-off value of the biomarker was determined as the sum of its maximum sensitivity and specificity.

To further validate the role of IP-10, a replication study involving an additional 40 KD patients and 57 non-KD febrile controls was performed. As shown in FIG. 2 (upper left panel), this study also showed a significant increase in the IP-10 levels in KD patients compared to those in the febrile controls. When the data from the replication study were combined with those of the discovery study (combined studies), the IP-10 level was significantly elevated in 77 KD patients (3,587±210.2 pg/mL) compared to the 77 non-KD febrile controls (921±106.2 pg/mL) (values in KD patients vs. values in non-KD febrile controls, p value=$2.8 \times 10^{-20}$). See FIG. 2 (upper right panel).

To further confirm the role of IP-10 as a biomarker in KD diagnosis, ROC curve analyses were performed using values of IP-10 from the combined studies. IP-10 showed an extremely high area under the curve (AUC) values of 0.94 (95% confidence interval, 0.9055-0.9778) when non-KD febrile patients were used as the controls. See FIG. 2 (lower panel). With a plasma IP-10 level of 1,318 pg/mL as the optimal cut-off value, as defined by the sum of maximum sensitivity and specificity, IP-10 showed a high sensitivity (100%) and specificity (77%) compared to the non-KD febrile controls. See FIG. 2 (lower panel).

Blinded Validation Study

Figure 3:
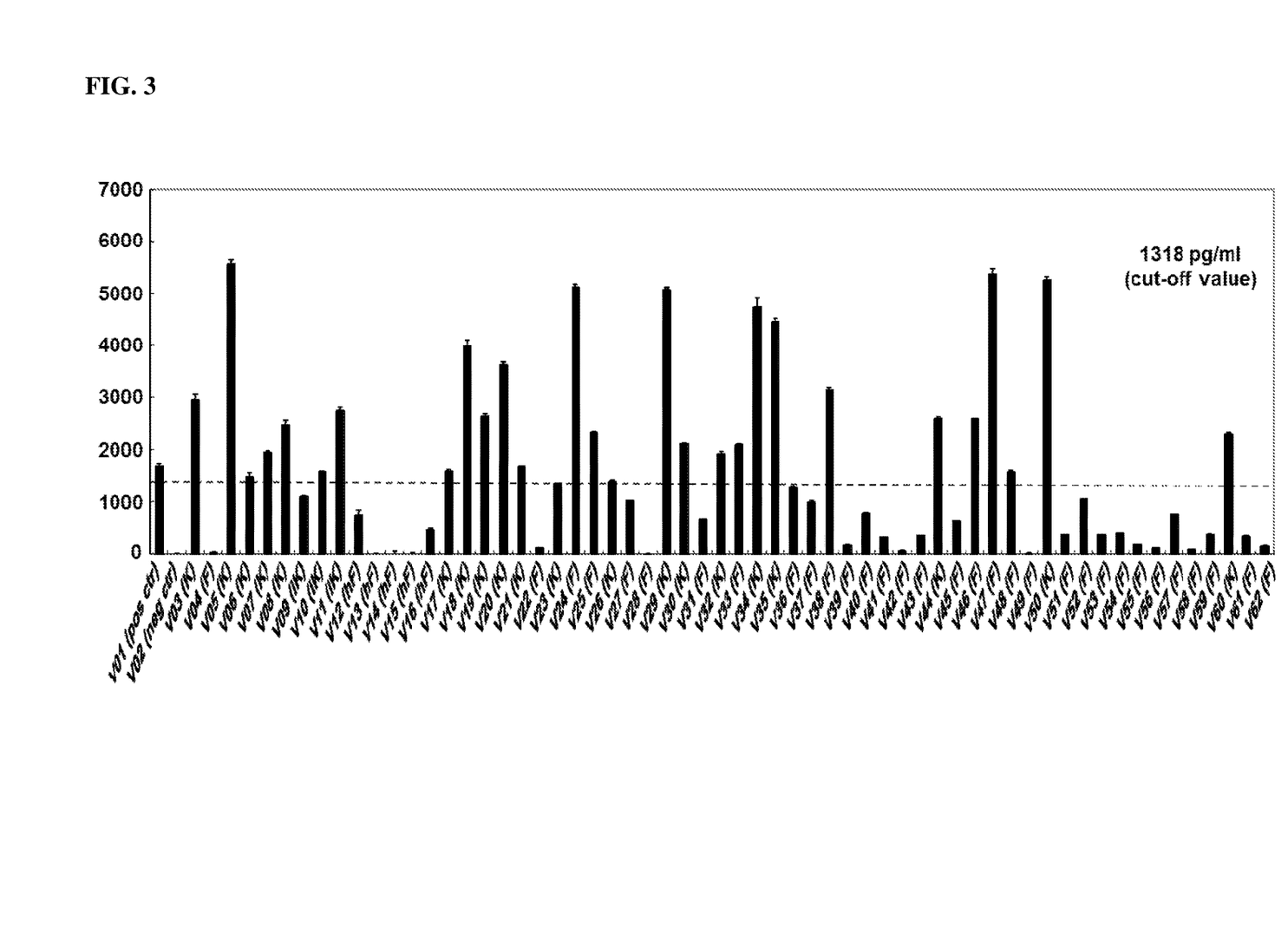

The final study phase was conducted using plasma samples from 60 children who were suspected with KD. The plasma IP-10 levels were measured in samples labeled in a blinded fashion, and the results were un-blinded and analyzed. Using a cut-off value of 1,318 pg/mL, 29 samples were IP-10 positive and 31 were IP-10 negative. KD was successfully diagnosed in 22 of the 29 IP-10 positive samples (including 2 cases of iKD); the remaining 7 samples were diagnosed with a non-KD fever. See FIG. 3. Of the 31 IP-10 negative samples, 30 were from non-KD febrile controls and 1 was from an iKD patient. Overall, the IP-10 cut-off value of 1,318 pg/mL showed good ability to distinguish between 23 KD patients and 37 non-KD febrile controls (sensitivity, 96% [22/23]; specificity, 81% [30/37]).

Figure 4A:
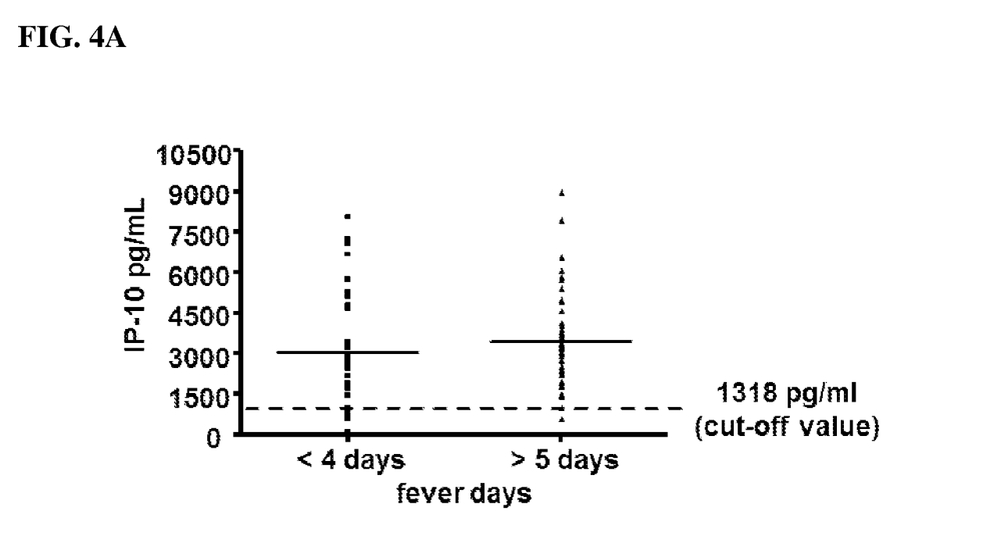
FIG. 4A is a dot plot showing IP-10 plasma levels in KD patients with blood obtained <4 days (mean, 3.4±0.90 days; range, 1-4 days) from the onset of fever or >5 days (mean, 6.0±1.05 days; range, 5-8 days) from the onset of fever. Each dot represents the average of 3 analyses with variation <5% (standard deviation/average) from a single individual.

Association of Plasma IP-10 Levels with Fever Duration and Intravenous Immunoglobulin Treatment To determine whether increased IP-10 levels could be detected during the early stage of KD, 37 KD samples obtained within 4 days of onset of fever (mean, 3.4±0.90 days; range, 1-4 days) were examined, and the results were compared with those of 46 samples obtained at a later stage of the disease (mean, 6.0±1.05 days of the onset of fever; range, 5-8 days). IP-10 levels were increased significantly in the early disease stage (3,054±331.0 pg/mL). See FIG. 4A. Using 1,318 pg/mL as the optimal cut-off value, 81% (30) of the 37 KD patients were identified as being in the very early stage (<4 days), while 96% (44) of the 46 KD patients were in the acute stage (>5 days).

Figure 4B:
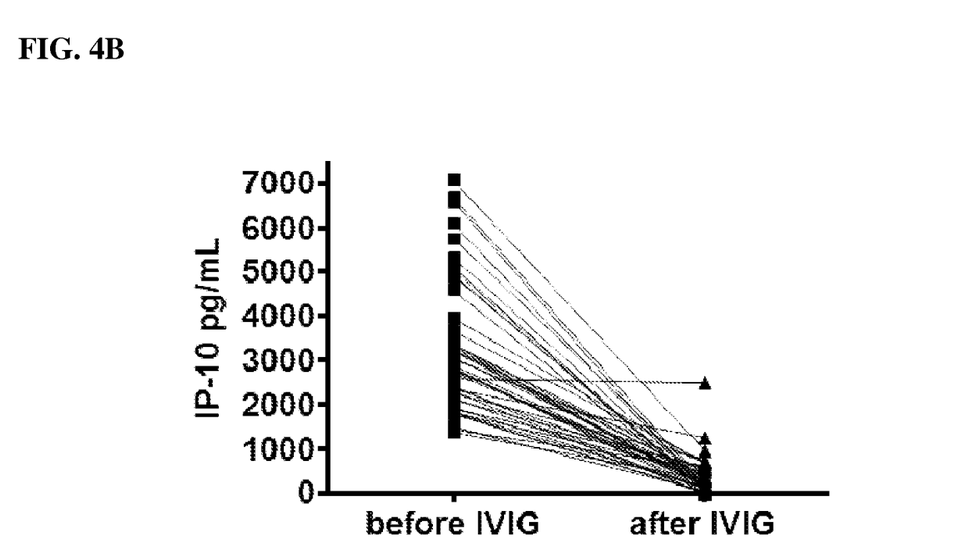
FIG. 4B is a graph showing plasma IP-10 levels before and 1 week after IVIG treatment in 45 patients with KD.

IP-10 levels were also examined in 45 patients before and 1 week after the initiation of IVIG treatment. High IP-10 levels before treatment returned to normal with IVIG treatment (before treatment, 3,323±224.9 pg/mL; after treatment, 348±64.8 pg/mL), except in 1 KD patient who was resistant to the first round of IVIG treatment and required a second course of therapy. See FIG. 4B.

Cell Surface Chemokine Receptor CXCR3 in T Cells

Figure 5:
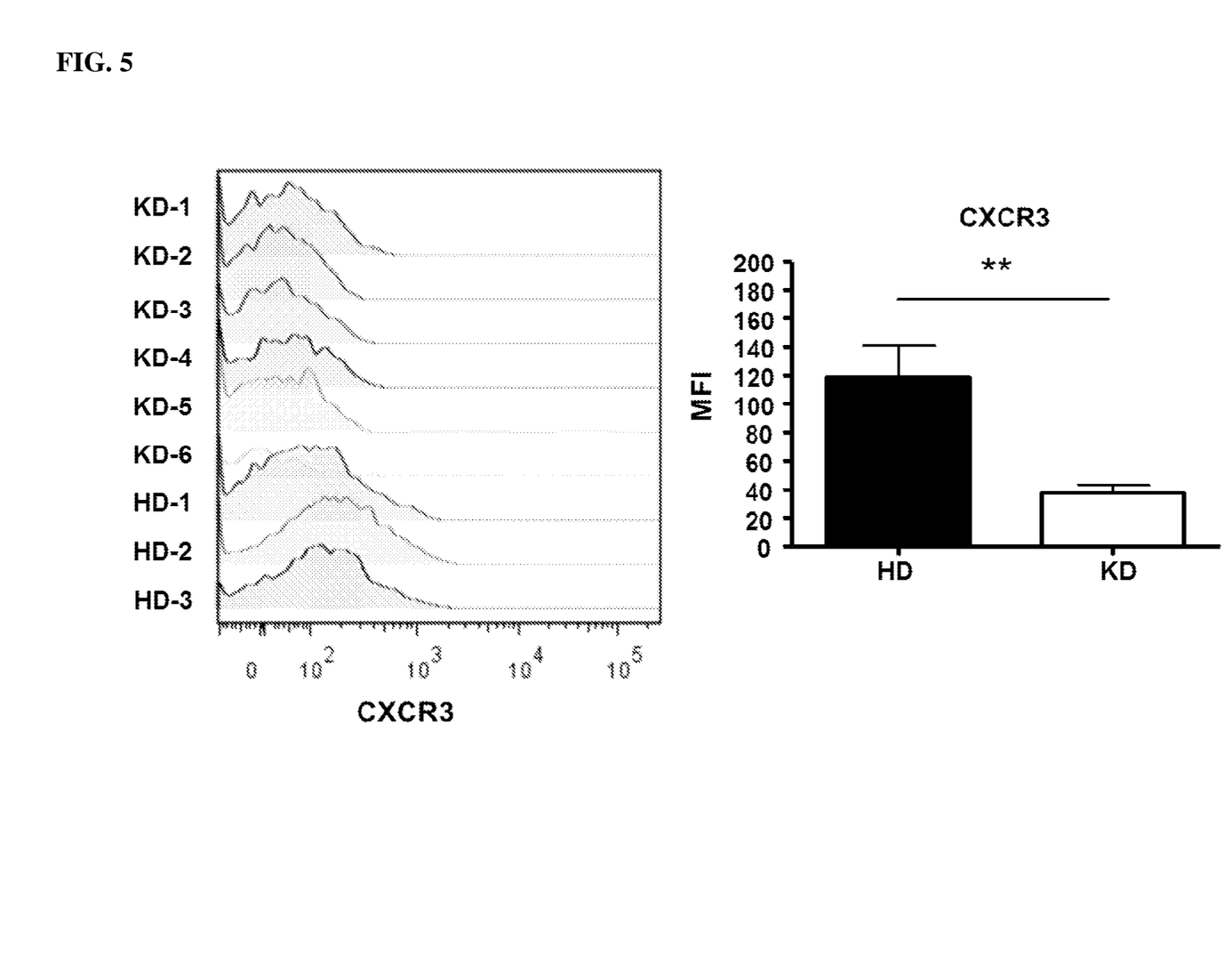
FIG. 5 is a set of graphs showing cell surface chemokine receptor CXCR3 in T cells of patients with acute KD. Left panel: Open curves indicate fluorescence activated cell sorter histogram plots of CD3+ T cells stained with anti-CXCR3 antibody. Patients KD-1 to KD-6 were in the acute stage of KD. HD indicates healthy donors. Right panel: A bar graph that summarizes the mean fluorescence intensity of CXCR3 in CD3+ T cells from 3 healthy donors and 6 patients with acute KD. **, p<0.01, unpaired Student's t-test.

IP-10 downregulates the cell surface chemokine receptor CXCR3 in T cells. To determine the downstream effect of increased IP-10 levels in KD patients, the cell surface expression of CXCR3 in T cells of 6 KD patients was analyzed. The mean fluorescence intensity (MFI) of $CD3^+$ T cells was measured, and there was a 3.3-fold decrease in MFIs in acute-stage KD patients compared with the MFIs of 3 healthy donors. See FIG. 5. In the recovery stage, the expression levels of CXCR3 were restored to normal (data not shown).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

A number of embodiments have been described. Nevertheless, it will be understood that various modifications may be made without departing from the spirit and scope of the invention. Accordingly, other embodiments are within the scope of the following claims.

The invention claimed is:

1. A method of diagnosing and treating Kawasaki disease in a subject, the method comprising:
   detecting a level of MPIF-1 in a plasma sample from a subject suspected of having Kawasaki disease, the level of MPIF-1 being higher than a cut-off MPIF-1 level, wherein the cut-off MPIF-1 level is an MPIF-1 level determined based on plasma MPIF-1 levels in febrile subjects without Kawasaki disease; and
   administering a treatment for Kawasaki disease to the subject, wherein the treatment is intravenous immunoglobulin (IVIG).

2. The method of claim 1, wherein the detecting step is carried out by an immune assay.

3. The method of claim 2, wherein the immune assay is ELISA, protein array, flow cytometry, multiplex immunoassays built on magnetic beads, Western blot, dot blot, or ELISPOT.

4. The method of claim 1, wherein the sample is obtained within 0 to 10 days of the onset of a fever in the subject.

5. The method of claim 4, wherein the sample is obtained within 4 days of the onset of a fever in the subject.

6. The method of claim 4, wherein the Kawasaki disease is incomplete Kawasaki disease.

7. The method of claim 1, further comprising:
   obtaining a second plasma sample from the subject after the treatment is administered;
   detecting a second level of MPIF-1 in the second sample; and
   continuing the treatment or administering a different treatment for Kawasaki disease if the second MPIF-1 level in the second sample is higher than the MPIF-1 cut-off level.

8. The method of claim 7, wherein the different treatment for Kawasaki disease includes a steroid.

* * * * *